United States Patent [19]
Grimes et al.

[11] Patent Number: 5,821,129
[45] Date of Patent: Oct. 13, 1998

[54] MAGNETOCHEMICAL SENSOR AND METHOD FOR REMOTE INTERROGATION

[76] Inventors: Craig A. Grimes, 525 McCalls Mill Rd., Lexington, Ky. 40515; William R. Seitz, 115 Madbury Rd., Durham, N.H. 03824

[21] Appl. No.: 799,607

[22] Filed: Feb. 12, 1997

[51] Int. Cl.[6] .................................................. G01N 27/74
[52] U.S. Cl. .......................... 436/151; 324/204; 324/219; 324/229; 324/230; 422/57; 422/68.1; 422/83; 436/149; 436/150; 73/DIG. 2
[58] Field of Search .................................... 436/148, 149, 436/150, 151; 422/68.1, 83, 57; 324/345, 204, 219, 229, 230; 73/DIG. 2

[56] References Cited

U.S. PATENT DOCUMENTS

| | | |
|---|---|---|
| 3,744,296 | 7/1973 | Beltzer . |
| 4,069,714 | 1/1978 | Spewock et al. . |
| 4,173,975 | 11/1979 | DeLong et al. . |
| 4,812,758 | 3/1989 | Yamashita et al. . |
| 4,841,244 | 6/1989 | Chambers . |
| 5,008,620 | 4/1991 | Nonaka et al. . |
| 5,348,761 | 9/1994 | Mitter et al. . |
| 5,355,714 | 10/1994 | Suzuki et al. . |
| 5,403,700 | 4/1995 | Heller et al. . |
| 5,502,381 | 3/1996 | Saitou . |
| 5,510,172 | 4/1996 | Araki et al. . |
| 5,514,337 | 5/1996 | Groger et al. . |

*Primary Examiner*—Jan Ludlow
*Attorney, Agent, or Firm*—King and Schickli

[57] ABSTRACT

A magnetochemical sensor for continuous and in-situ sensing of a given chemical species/stimuli includes two magnetically-soft magnetic film layers and a chemical transduction layer that shrinks or swells in the presence of that given chemical species/stimuli. The magnetic switching characteristics of the sensor are dependent upon the thickness of the chemical transduction layer. A method for remotely interrogating the magnetic switching characteristics of the sensor is also provided. In the method, magnetic flux detecting coils are utilized to monitor the sensor.

18 Claims, 4 Drawing Sheets

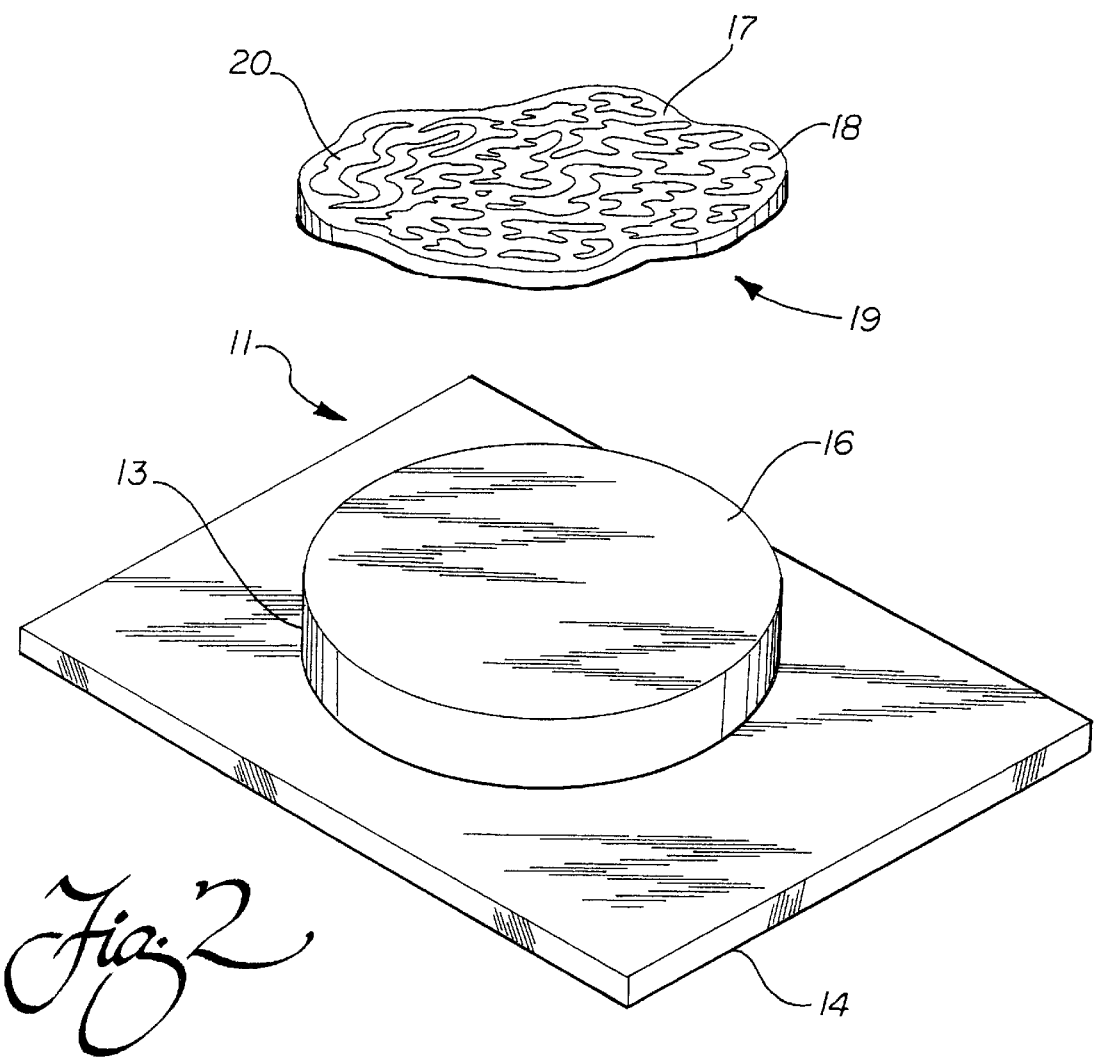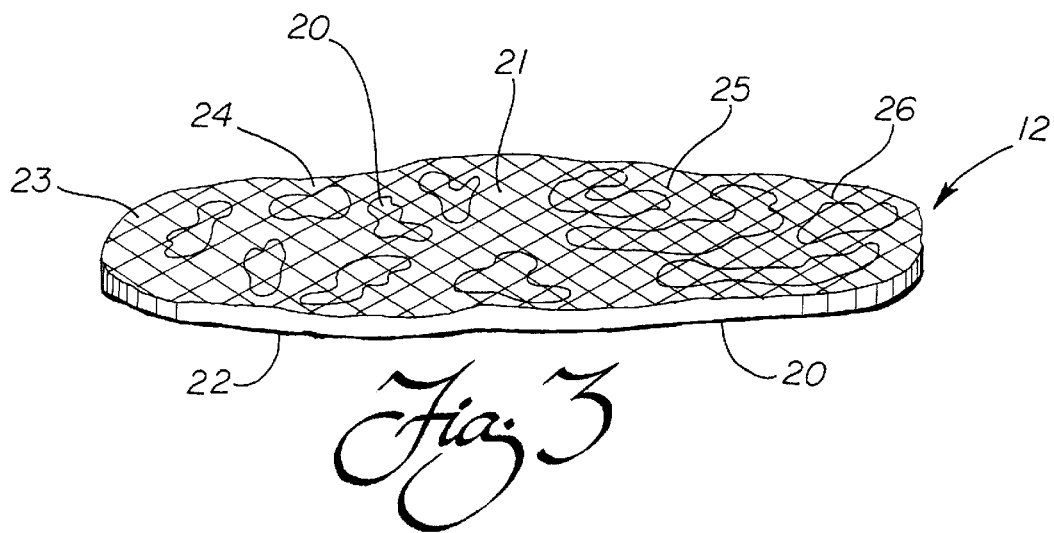

MAGNETOCHEMICAL SENSOR AND METHOD FOR REMOTE INTERROGATION

TECHNICAL FIELD

The present invention relates generally to a chemical sensor; and more particularly to a chemical sensor for remote, continuous, and in-situ detection and measurement of various chemical species/stimuli.

BACKGROUND OF THE INVENTION

Environmental related concerns are becoming more and more important to our society today than at any time in our history. Governments and environmental regulatory agencies are continually promulgating new statutes and regulations which require precise detection and monitoring of numerous chemicals. In some instances, the levels of detection and monitoring required are simply not attainable with present day sensors. In response to these new statutes and regulations, various types of chemical sensors have been developed to detect and measure such things as air/water pollutants and chemical concentrations.

For example, U.S. Pat. No. 5,514,337 to Groger et al. teaches the use of chemical and resonant sensors in determining chemical concentrations of unknown chemical analytes. These sensors are based upon the interaction of an excitation electromagnetic signal with a chemically sensitive film. Specifically, the '337 sensor is comprised of a chemically sensitive film and primarily either an eddy current detector or a resonant resistance-inductance capacitance (RLC) circuit.

In operation, the film is exposed to the chemical analyte, thereby altering its electrical properties. The altered properties are detected as a change in the impedance of an eddy current probe in the vicinity of the film or in the change of the resonance frequency of an adjustable tuned circuit in the vicinity of the film. One disadvantage with these particular detecting circuits is the requirement that they be located in close proximity to the conducting polymer film.

A moisture resistive sensor described in U.S. Pat. No. 5,348,761 to Mitter et al. utilizes a swellable plastic having conductive additives. The '761 reference teaches the use of polyimides, copolyimides, and additional materials for use as the swellable component and carbon black, metal dust or the like as the conductive additives. In operation, the sensor swells in response to moisture, thereby increasing the relative distance between the additives and the conductivity so that a positive change in resistance is observed with increasing moisture. Again however, in each embodiment of the sensor described connecting wires are attached to electrodes for monitoring the sensor. The inability to provide remote detection and monitoring severely limits the usefulness of the sensor.

U.S. Pat. No. 5,083,112 to Piotrowski et al. discloses a remotely interrogable multi-layer thin-film marker for use with electronic article surveillance (EAS) systems. Magnetic-type, RF, and microwave based EAS systems are commonly used to deter or prevent the theft of such commercial items as books, cassette tapes, CD ROM's, and clothing. The magnetic-type EAS system typically comprises a means for producing a magnetic field, markers adapted to be affixed to the articles to be protected, and a detecting means for producing an appropriate alarm signal.

The thin-film marker used with the EAS systems as described in the '112 reference comprises a laminate of a plurality of magnetic thin-films, deposited on a flexible substrate, wherein each of the magnetic thin-films is separated from an adjacent film by a non-magnetic thin-film. Each of the magnetic thin-films is formed of a composition exhibiting high permeability and low coercive force, so as to enable a state of magnetization therein to reverse upon exposure to the relatively low intensity alternating magnetic fields associated with these systems. The non-magnetic thin-films are sized to allow magnetostatic coupling between the adjacent magnetic films, but are sufficiently thick to inhibit exchange coupling therebetween. This allows the magnetization states of all of the magnetostatically coupled films to reverse as a single entity upon exposure to an alternating magnetic field. While this system allows remote interrogation, it does not allow the sensing of a selected chemical species.

Accordingly, a need is identified for a chemical sensor having remote, continuous, and in-situ chemical species detection and measurement capabilities.

SUMMARY OF THE INVENTION

Accordingly, it is a primary object of the present invention to provide a novel magnetochemical sensor that is particularly adapted for sensing a given chemical species/stimuli and includes concepts and features that are designed to overcome the limitations of the prior art.

Another object of the present invention is to provide a remote and in-situ magnetochemical sensor that is particularly adapted to eliminating the need for external electrical connections.

It is another object of the present invention to provide a remote, continuous, and in-situ magnetochemical sensor that is inexpensive to manufacture and is therefore capable of use on a disposable basis.

It is yet another object of the present invention to provide a remote, continuous, and in situ magnetochemical sensor that is durable.

Yet another object of the present invention is to provide a remote, continuous, and in situ magnetochemical sensor having magnetically-soft magnetic particles interspersed throughout a chemical transduction layer sensitive to a selected chemical species.

Still another object of the present invention is to provide a method for remotely, continuous, and in situ monitoring the concentration of a chemical species/stimuli in an environment.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, a novel magnetochemical sensor is provided for sensing a given chemical species/stimuli. The magnetochemical sensor includes two magnetic thin film layers separated by a non-magnetic spacer layer. More specifically, the non-magnetic spacer layer is made from a chemical transduction material which shrinks or swells in the presence of a certain chemical species/stimuli. Preferably, the magnetic switching characteristics of the sensor are dependent upon the non-magnetic spacer layer thickness.

When placed within an alternating magnetic field the magnetization vector of the sensor periodically reverses directions, generating magnetic flux that can be detected as a series of voltage spikes in suitably located detecting coils. The general shape and magnitude of the voltage spikes are dependent upon how much the non-magnetic spacer layer thickness has changed in response to the presence of the chemical species/stimuli being monitored.

In accordance with one aspect of the present invention, changes in magnetic flux of the sensor are remotely interrogated and monitored to obtain the information inherent in the sensor. No physical connections such as wires, cables, or any direct connection are required to obtain the sensor information. This remote interrogation capability advantageously allows the sensors to be placed within areas which previously could not be monitored such as conductive enclosures, pipelines, hermetically sealed packages, gas tanks, animals, or even humans. Therefore, the sensor is ideally suited for monitoring such things as moisture levels in sealed containers, pollutants in enclosed pipes, carbon dioxide levels in food packages as well as gastric pH levels and glucose levels in animals and humans.

The remote interrogation and monitoring of the changes in the magnetic flux produced by the sensor are accomplished using proven interrogation and monitoring electronics. Magnetic identification marker systems, such as the EAS systems described above, are widely commercially used in the prevention of theft. These systems involve similar sensor interrogation and monitoring techniques which are known to be effective over a range of several meters.

Advantageously, it has been determined that thin spacer layers result in a magnetically coherent film with uniform switching characteristics. The spacer layer of the present invention includes a thin layer of a chemical transduction material. In another important aspect of the present invention, a thin spacer layer requires only a minimal use of material, thereby effectively reducing the overall cost of the sensor. Utilizing known methods of manufacturing, the sensors would likely cost less than $0.01 per unit. At this cost per unit, the sensors could easily be considered to be disposable despite their durability.

In yet another important aspect of the present invention, the two magnetic thin film layers can be covered with a protective or bio-compatible coating. This is accomplished with nominal effect on the performance of the sensor. This protective coating advantageously allows the sensors to be placed in an unlimited number of environmentally sensitive or hazardous areas such as exhaust pipes, flumes, chemical baths or even implanted within the body. Protecting the magnetic layer from direct contact with the chemical environment reduces the opportunity for oxidation or corrosion of the sensor which is therefore able to provide continuous in-situ operation over very long periods of time.

In accordance with another important aspect of the present invention, an alternate embodiment of the magnetochemical sensor includes magnetically-soft magnetic particles dispersed throughout the chemical transduction layer such that changes in the thickness of the chemical transduction layer alter the magnetic switching characteristics of the sensor dependent upon the surrounding concentration of the selected chemical species.

In a further aspect of the invention, in accordance with its objects and purposes, a method of remotely interrogating the sensor and monitoring or detecting the presence of a chemical species/stimuli includes the steps of providing a magnetochemical sensor, introducing the sensor into a chemical environment, providing an alternating magnetic field, introducing the sensor and the chemical environment into the magnetic field, detecting the magnetic flux which results from the periodic reversal of the magnetization vector of the sensor caused by the alternating magnetic field, and determining the concentration presence of the chemical species/stimuli according to the voltage magnitude of the detected magnetic flux.

Advantageously, it should be appreciated that this method of interrogating the sensor to monitor or determine the concentration presence of a chemical species/stimuli does not require any external connections. The sensor information is simply remotely monitored in-situ. Accordingly, the sensor and the monitoring of the sensor information is greatly simplified over prior art sensors and monitoring systems. The present method allows for continuous, in situ, and remote monitoring requiring significantly less time and effort and is more convenient for the individual performing the monitoring operations.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of still other different embodiments, and its several details are capable of modifications in various, obvious aspects all without departing from the invention. Accordingly, the drawings and descriptions will be regarded as illustrative in nature and not as restrictive.

BRIEF DESCRIPTION OF THE DRAWING

The accompanying drawings incorporated in and forming a part of the specification, illustrate several aspects of the present invention, and together with the description serve to explain the principles of the invention. In the drawings:

FIG. 2 is an exploded perspective view of a magnetic thin film layer on a glass slide;

FIG. 3 is a perspective view of a chemical transduction layer;

Reference will now be made in detail to the present preferred embodiment of the invention, an example of which is illustrated in the accompanying drawing.

DETAILED DESCRIPTION OF THE INVENTION

Figure 1:
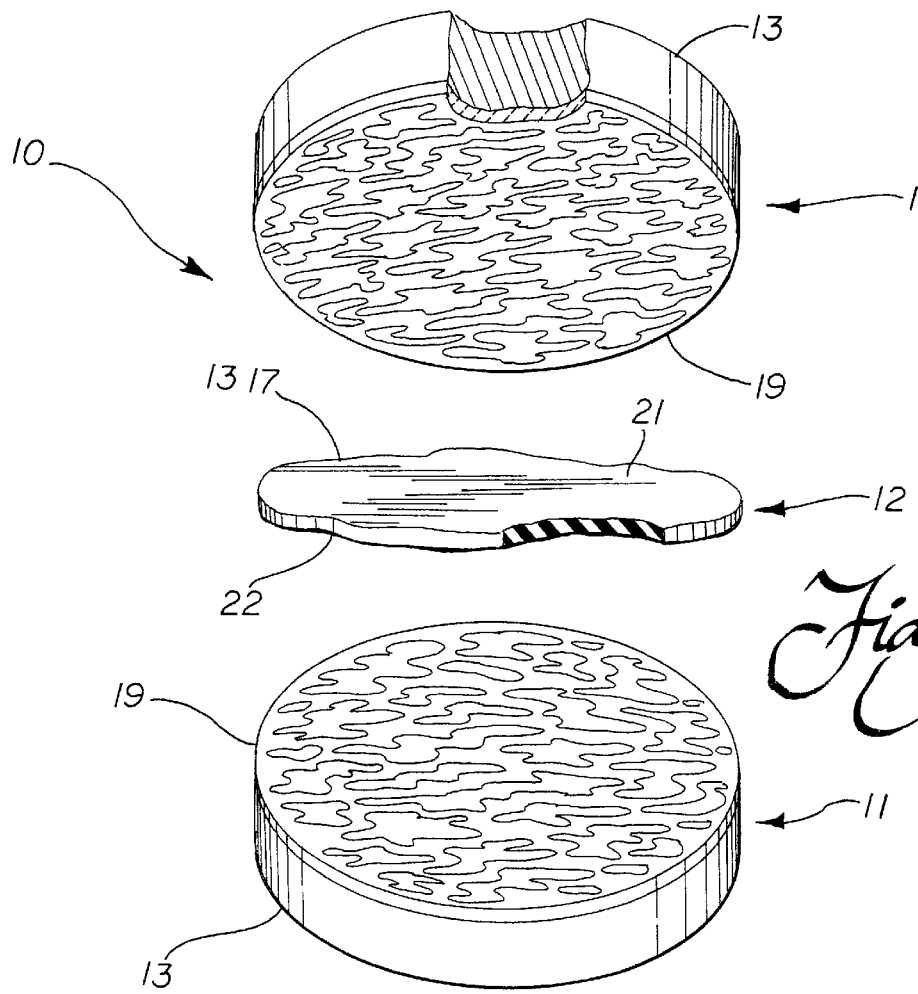
FIG. 1 is an exploded perspective view of the magnetochemical sensor of the present invention showing each layer of the sensor.

Reference is now made to FIG. 1 showing the magnetochemical sensor 10 of the present invention. The sensor 10 includes two magnetically-soft magnetic film layers 11, one layer being located on either side of a chemical transduction layer 12. For purposes of illustration and description, a pH sensor will be described in detail. It is to be understood, however, that this description is not intended to be exhaustive or to limit the invention to the precise form disclosed.

As will be discussed in more detail below, various chemical transduction layer materials can be used for differing sensor applications. In the sensor 10, the magnetic film layers 11 consist of two 18 mm diameter layers separated by a pH sensitive chemical transduction layer 12.

As best shown in FIG. 2, the magnetic film layers 11 primarily consist of a 100 nm single layer $Ni_{81}Fe_{19}$ thin film 13 RF sputtered onto a glass cover slide 14. $Ni_{81}Fe_{19}$ is a high flux, non-magnetorestrictive alloy having magnetic properties which advantageously do not change as a function of stress. The single layer $Ni_{81}Fe_{19}$ thin films 13 are deposited using a 3-target Perkin-Elmer 4410 RF sputtering machine. An equally effective method of depositing magnetic film layers is by vacuum evaporation or DC sputtering, or DC magnetron sputtering.

A top surface 16 of the thin films 13 is coated with a 5 nm $SiO_2$ layer 17. The $SiO_2$ layer 17 is similarly RF sputtered onto the top surface 16 of the thin film 13. The $SiO_2$ layer 17 is then treated with a 0.5% (v/v) aqueous solution 18 of 3-methacryloxypropyltrimethoxysilane adjusted to pH 3 with acetic acid to form a thin coating 19. The magnetic film layer 11 including the $Ni_{81}Fe_{19}$ thin film 13 and the thin coating 19 are then allowed to cure overnight at room temperature. This procedure chemically bonds a thin chemically reactive acrylate layer 20 onto the $SiO_2$ layer 17.

As best shown in FIG. 3, the transduction layer 12 consists of a polymer that is formed by reacting the monomers 2-(dimethylamino)ethyl methacrylate 23 and hydoxyethylmethyacrylate 24, with 3 mole-% ethylene glycol dimethacrylate crosslinking agent 25 and 0.85% (w/w) of azoisobutyrylnitrile (AIBN) 26 to initiate free radical polymerization. A chemically reactive acrylate layer 20 is also incorporated into the top and bottom surfaces 21, 22 of the chemical transduction layer 12 such that the transduction layer can be covalently bonded to the $SiO_2$ layer 17.

A polyacrylate polymer was chosen as the substrate polymer because it is flexible and easily prepared by thermal free radical polymerization. A variety of functional groups can be introduced onto polyacrylate polymer backbones to modify the selectivity of the transduction material for various analytes. Many polyacrylates are hydrophilic and swell in water so that the polymer network is permeable to aqueous analytes.

Another class of polymer that is well suited for use as the substrate polymer is derivatized polystyrenes. Numerous procedures exist for introducing functional groups onto polystyrene backbones. Clearly, other polymers which contain functional groups that selectively interact with the species causing the polymer to swell or shrink can also be substituted.

Next, as shown in FIG. 1, the bottom side 22 of transduction layer 12 is applied to the chemically modified top surface 16 of one of the $Ni_{81}Fe_{19}$ thin films 13. The chemically modified top surface 16 of the second $Ni_{81}Fe_{19}$ thin film 13 is next applied to the top side 21 of the transduction layer 12. An initiator is used to promote covalent bonding of the acrylate groups 20 in the top surface 16 and the top and bottom sides 21, 22 of the transduction layer 12.

Figure 4:
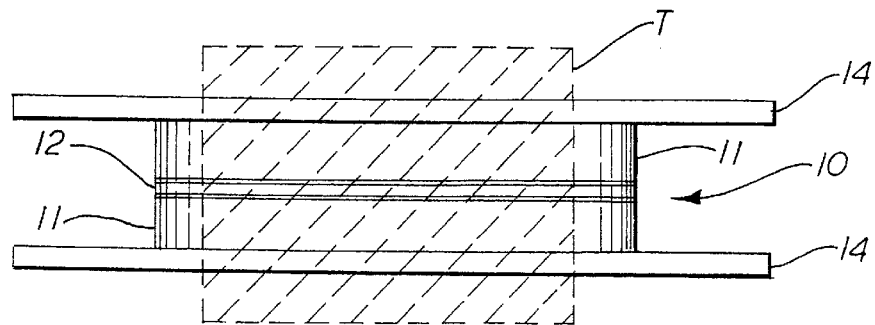
FIG. 4 is an elevational side view of a magnetochemical sensor mounted between glass slides and held in place with pressure sensitive tape.

As shown in FIG. 4, the sensor 10 is sandwiched between two glass slides 14 and covered with pressure sensitive Teflon tape (T). The sensor 10 is then placed in an oven at 70 degrees Centigrade for four hours to initiate polymerization. At the end of this period, the glass slides 14 and tape T are removed from the resultant sensor 10.

An equally effective method for adhering the $Ni_{81}Fe_{19}$ thin films 13 to the transduction layer 12 is to apply a soft, non-hardening glue between the top surface 16 of the $Ni_{81}Fe_{19}$ thin films 13 and the top and bottom sides 21, 22 of the transduction layer.

Figure 5:
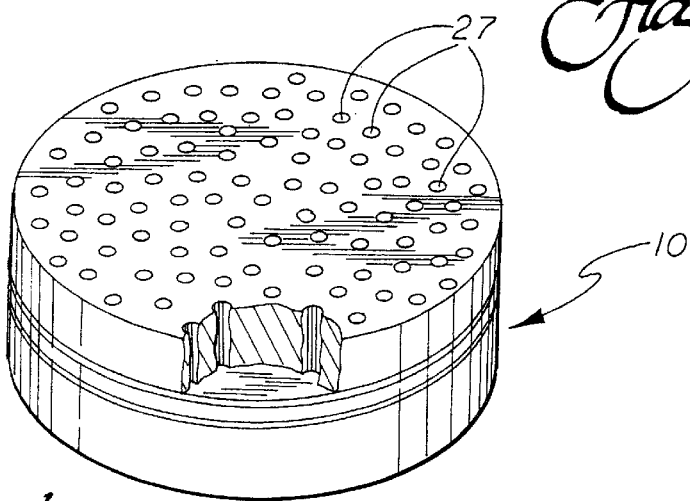
FIG. 5 is a perspective view of a magnetochemical sensor having a pattern of holes in the magnetic thin film layers.

In an alternate embodiment of the present invention shown in FIG. 5, small holes 27 are introduced through the thin films 13 to increase the overall response time of the sensor 10. The use of porous thin films 13 increases the exposed surface area of the transduction layer 12. The response time t of a sensor is given by the equation:

$$t = L^2/D \tag{1}$$

where L is the diffusion distance and D is the diffusion coefficient. Accordingly, introducing 2 micron holes spaced 10 microns apart will result in a response time of approximately 0.01 seconds. Of course by varying the spacing patterns of the holes, changes in the response times of the sensor can be achieved. An increase in the exposed surface area of the transduction layer 12, for example, can also be accomplished by patterning the sensor into a collection of smaller regions, or depositing the magnetic film onto a porous substrate.

Figure 6:
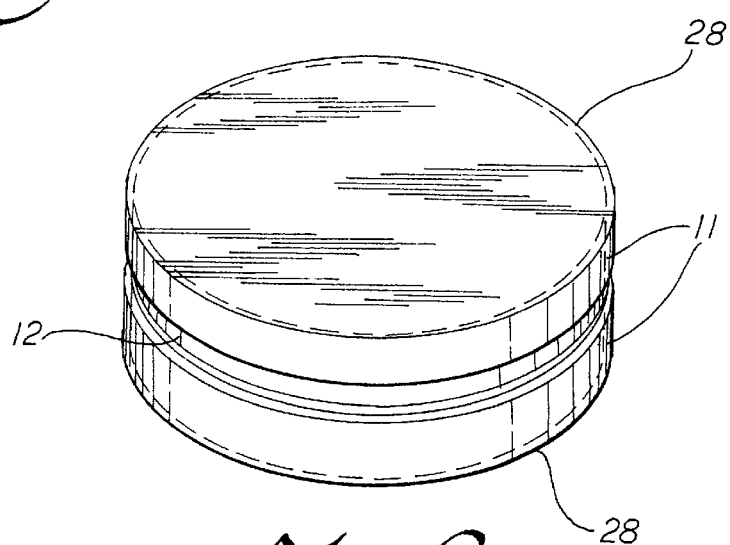
FIG. 6 is a perspective view of a magnetochemical sensor having a protective coating around the magnetic thin film layers.

In another alternate embodiment of the present invention as shown in FIG. 6, a protective or biocompatible coating 28 is applied to the magnetic film layers 11. The coating 28, made from material such as titanium or the like, allows the sensor 10 to be placed within environmentally sensitive or hazardous areas without adversely affecting the performance of the sensor 10.

Figure 10:
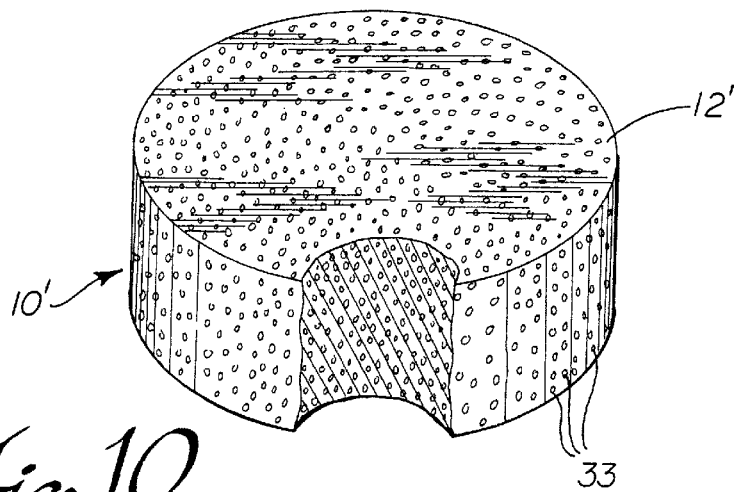
FIG. 10 is a perspective view of an alternate embodiment of a magnetochemical sensor having magnetically-soft magnetic particles interspersed throughout a chemical transduction layer.

In a further alternate embodiment of the present invention as shown in FIG. 10, sensor 10' includes a chemical transduction layer 12' having magnetically-soft magnetic particles 33 interspersed throughout such that changes in the thickness of the chemical transduction layer alter the magnetic switching characteristics of the sensor dependent upon the surrounding concentration of the selected chemical species. As will be discussed in more detail below, various chemical transduction layer materials can be used for differing sensor applications.

The method for remotely interrogating and monitoring the presence of a chemical stimuli species in an environment will now be described in detail. In a first step, a magnetochemical sensor 10 is provided. Magnetochemical sensors, such as the ones described above, are based upon the basic magnetic flux detection principle known as Faraday's Law. According to Faraday's Law a time varying magnetic flux generates a voltage in detecting coils according to:

$$d\Psi/dt = -V \tag{2}$$

where V is the induced voltage, t is time, and $\Psi$ is the total magnetic flux. The faster the flux changes with respect to time the greater the magnitude of the generated voltage spike.

Next, the sensor 10 or 10' is introduced into the chemical environment 29 to be monitored and the sensor and chemical environment are subjected to an alternating magnetic field (H), thereby creating a magnetic flux. The total magnetic flux is the product of the magnetic flux density (B) and the cross sectional area of the detecting coil. Magnetic flux density (B) is the sum of flux due to the applied magnetic field, and flux associated with the magnetization (M) of a magnetic material or alloy, in this instance the thin films 11. For ferromagnetic materials, the flux associated with a reorienting magnetization vector can be thousands of times greater than that of an applied magnetic field, and it is upon this flux change that the sensor is monitored.

In most films the magnetization vector of the film lies along a particular direction in the basal plane, meaning the film is magnetically anisotropic. The application of a magnetic field acts to orient the polycrystalline regions, or domains, in the direction of the applied field. When all domains of the film are oriented in the same direction it is magnetically saturated. The magnitude of the applied magnetic field necessary to saturate the film is called the coercive force (Hc). In response to an alternating magnetic field that has an amplitude greater than Hc, the magnetization vector of the magnetic sample will alternately reverse direction with a corresponding change in the magnetic flux, cycling through the magnetic hysteresis loop.

Although the total magnetic moment of a film is fixed and largely dependent upon the alloy, how the magnetic flux of a given film changes in response to an applied magnetic field is dependent upon how the film is made and the relative orientation between the magnetization vector and the applied field.

Figure 7:
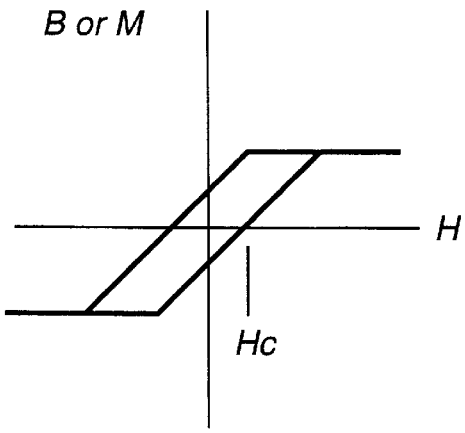
FIG. 7 is an illustrative drawing of a low frequency BH hysteresis loop for a film with the magnetization vector oriented perpendicular to a time varying sinusoidal magnetic field H.

FIG. 7 is an illustrative drawing of a low frequency BH hysteresis loop for a film with the magnetization vector oriented perpendicular to a time varying sinusoidal magnetic field (H). The magnetization responds linearly to the applied field until the sample reaches saturation. For this orientation, the change in flux with time is a relatively small quantity, and hence the voltage spike that is induced in a set of detecting coils is also small. Upon saturation the change in magnetic flux with time is essentially zero. Therefore, for this relative orientation the detected output is a series of relatively small amplitude voltage rises.

Figure 8:
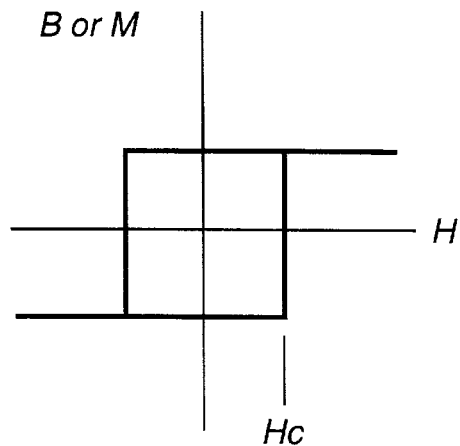
FIG. 8 is an illustrative drawing of the hysteresis loop for a film with the magnetization vector oriented parallel to the applied time varying magnetic field.
Figure 9:
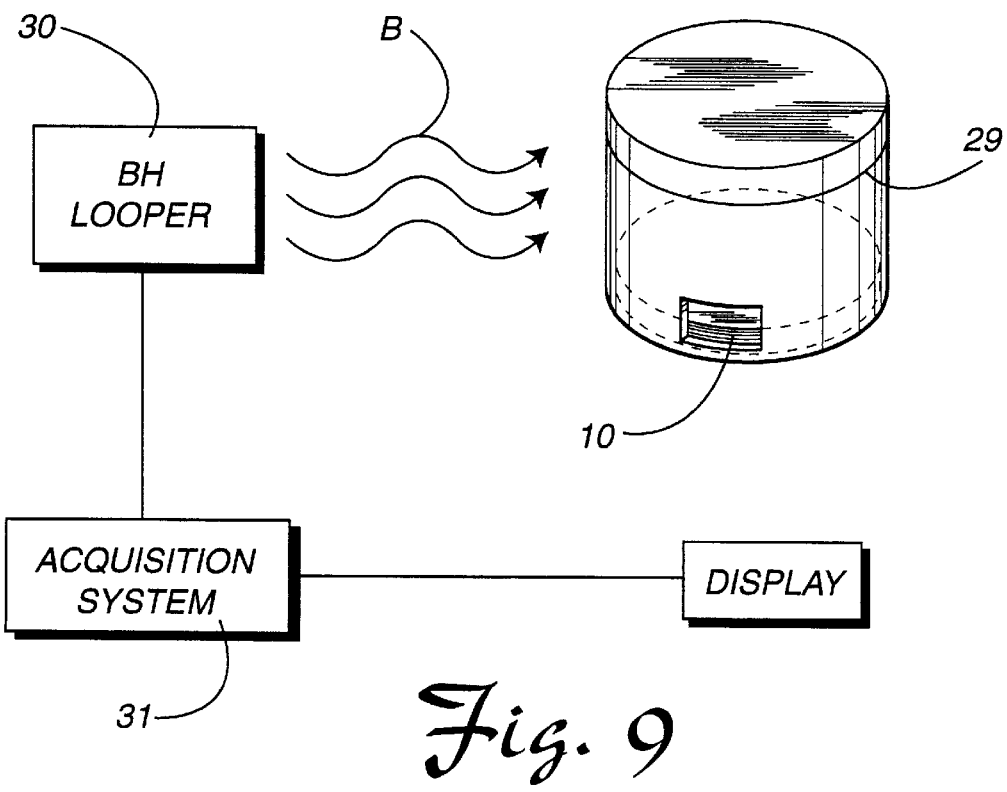
FIG. 9 is a block diagram of the remote monitoring means.

As shown in FIG. 8, the magnetization, for a film having a magnetization vector oriented parallel to the applied time varying magnetic field, responds non-linearly to the applied field, coherently switching at a field amplitude equal to the coercive force. The change in flux with time is large, and hence the voltage spike that is induced in a set of detecting coils is also large. The response to an incident, or interrogating, ac magnetic field is a series of sharp, large amplitude voltage spikes. In the last step of the present method, detection electronics are used to identify such a film in one of three ways: (1) voltage spike amplitude, (2) time duration of spike, and (3) time interval between spikes. Although an isotropic marker with a magnetic signature like that of FIG. 8 would be ideal, in practice it has been found that isotropic magnetic films generally have BH loops similar to that of FIG. 7, making it difficult to identify them from background noise.

All magnetic materials that pass through an interrogating field undergo some change in flux, and consequently generate some voltage signal in the detecting coils. However, unless the material has a BH loop like that of FIG. 8, and a coercive force less than the amplitude of the interrogating field, the signal is small. Magnetic materials with such properties do not generally occur unless specifically designed and fabricated for that purpose.

Magnetic identification markers, for example, are fabricated to be magnetically soft, having a low coercive force value, typically −0.2 Oe, and have a BH loop like that of FIG. 8. The detection technology for use with these markers has advanced to the point where a well behaved 2.5 cm×2.5 cm×1 mm thick ferromagnetic film, passing through an interrogating magnetic field, can be continuously, unintrusively, non-destructively, and inexpensively monitored up to several meters away.

In the present invention, a low frequency BH looper 30 has been built that allows for film characterization through either measurement of the BH loop or generated voltage waveform. Attached to the BH looper is a computer based acquisition system 31 and display monitor 32 or printer that measures and stores the sensor response signal associated with changes in the magnetic flux. Characterization of the sensor 10 can be accomplished at set time intervals or during continuous operation.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, a humidity sensor can be prepared using a hydrophilic polymer as the chemical transduction layer. The remote capabilities of the sensor provide for the opportunity of monitoring the interior moisture level of a sealed package.

Likewise, a sensor utilizing a hydrophilic basic polymer as the transduction layer can be used to detect carbon dioxide and therefore, bacterial contamination in a sealed container. Carbon dioxide partitions into the hydrated polymer where it reacts with water forming carbonic acid, $H_2CO_3$. Carbonic acid donates a hydrogen ion to the basic polymer, thereby introducing a charge onto the polymer backbone. This in turn increases the affinity of the polymer for water and causes it to swell by absorbing water vapor.

The measurement of gastric pH can be accomplished using a hydrophilic protonatable polymer as the transduction layer.

Other possible applications include but are not limited to remotely sensing water in gasoline tanks using hydrophilic polymers and detecting hydrogen sulfide in air. For example, a poly(acrylic acid) can lose a proton to form poly(acrylate), thereby introducing a negative charge onto the polymer causing it to have a higher affinity for water and to swell by absorbing the water vapor. Gas phase hydrogen sulfide can be detected by utilizing a thin layer of copper metal as the transduction layer. Hydrogen sulfide reacts rapidly with copper to form CuS which is larger in volume than Cu metal. This irreversible process results in the sensor acting as a dosimeter.

Also, the detection of heavy metal ions such as Pb(II) or Cu(II) in aqueous media can be accomplished using a polymer that serves as a ligand as the transduction layer. This type of sensor can be used to screen waste water streams from industrial and municipal sources or metal ion levels in pipelines.

Additionally, hydrazine and its derivatives can be detected using a thin layer of aldehydes which form hydrazones in the presence of hydrazine. The process involves the replacement of the oxygen of the aldehyde group with three atoms (N-N-H) in the hydrazone causing a detectable increase in volume. Again, this process is irreversible and results in the sensor acting as a dosimeter.

The preferred embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A method for remotely monitoring the concentration of a chemical species in an environment comprising the steps of:

providing a magnetochemical sensing means having a magnetization vector;

said magnetochemical sensing means being constructed from at least two magnetically-soft magnetic film layers and at least one chemical transduction layer between said magnetically-soft magnetic film layers;

introducing said sensing means to said environment;

providing an alternating magnetic field generating means;

introducing said sensing means in said environment to an alternating magnetic field produced by said generating means; and providing a magnetic flux detection means;

whereby a magnetic flux resulting from periodic reversal of the magnetization vector of said sensing means is detected by the detection means and the presence or concentration of said chemical species in said environment is determined based upon the magnitude of said magnetic flux; and whereby changes in the thickness of said transduction layer alter said magnetic switching characteristics of said sensing means dependent upon the surrounding concentration of said chemical species in said environment.

2. The method of claim 1, including coating said magnetically-soft magnetic film layers with a bio-compatible coating whereby said sensing means can be placed within environmentally sensitive areas and said magnetically-soft magnetic film layers are protected from the environmental surroundings.

3. The method of claim 1, including selecting a chemically responsive polymer that selectively interacts with said selected chemical species to be detected for said chemical transduction layer.

4. A method for remotely monitoring the concentration of a chemical species in an environment comprising the steps of:

providing a magnetochemical sensing means having a magnetization vector;

said magnetochemical sensing means being constructed chemical transduction layer sensitive to a selected chemical species, said transduction layer having magnetically-soft magnetic particles interspersed throughout;

introducing said sensing means to said environment;

providing an alternating magnetic field generating means;

introducing said sensing means in said environment to an alternating magnetic field produced by said generating means; and providing a magnetic flux detection means;

whereby a magnetic flux resulting from periodic reversal of the magnetization vector of said sensing means is detected by the detection means and the presence or concentration of said chemical species in said environment is determined based upon the magnitude of said magnetic flux; and whereby changes in the thickness of said chemical transduction layer alter said magnetic switching characteristics of said sensing means dependent upon the concentration of said selected chemical species.

5. A magnetochemical sensing apparatus comprising:

a sensing means including at least two magnetically-soft magnetic film layers, and at least one chemical transduction layer sensitive to a selected chemical species disposed between said magnetically-soft magnetic film layers;

a generator means for generating an alternating magnetic field; and a detector means for detecting magnetic flux;

whereby changes in the thickness of said chemical transduction layer alter magnetic switching characteristics of said sensing means exposed to said alternating magnetic field and measured by said detector means dependent upon surrounding concentration of a selected chemical species.

6. A magnetochemical sensor having predetermined magnetic switching characteristics including a magnetization vector, said magnetization vector periodically reversing directions when placed in an alternating magnetic field thereby generating a magnetic flux, said magnetic flux being detectable as a series of voltage spikes comprising:

at least two magnetically-soft magnetic film layers; and at least one chemically responsive polymer layer having a thickness and sensitive to a selected chemical species, alternatingly disposed between said magnetically-soft magnetic film layers;

the thickness of said chemically responsive polymer layer varying dependent upon the surrounding selected chemical species, whereby changes in the thickness of said chemically responsive polymer layer alter the magnetic switching characteristics of said sensor.

7. The magnetochemical sensor of claim 6, further comprising a bio-compatible coating substantially surrounding said magnetically-soft magnetic film layers whereby said sensing apparatus can be placed within environmentally sensitive areas and said magnetically-soft magnetic film layers are protected from the environmental surroundings.

8. The magnetochemical sensor of claim 7, wherein said bio-compatible coating is titanium.

9. The magnetochemical sensor of claim 6, wherein said chemically responsive polymer is a lightly crosslinked polymer.

10. The magnetochemical sensor of claim 6, wherein said chemically responsive polymer is a polyacrylate.

11. The magnetochemical sensor of claim 6, wherein said chemically responsive polymer is a derivatized polystyrene.

12. The magnetochemical sensor of claim 6, wherein said chemically responsive polymer is a copolymer of an acrylate and a derivatized styrene.

13. The magnetochemical sensor of claim 6, wherein said magnetically-soft magnetic film layers are a magnetically soft alloy of iron.

14. The magnetochemical sensor of claim 6, where in said magnetically-soft magnetic film layers are a magnetically soft alloy of nickel.

15. The magnetochemical sensor of claim 6, wherein said magnetically-soft magnetic film layers are a magnetically soft alloy of cobalt.

16. The magnetochemical sensor of claim 6, wherein said magnetically-soft magnetic film layers are a magnetically soft alloy of gadolinium.

17. The magnetochemical sensor of claim 6, wherein said chemically responsive polymer layer has a substantially uniform thickness.

18. The magnetochemical sensor of claim 6, wherein said chemically responsive polymer layer is irreversibly sensitive to said selected chemical species;

whereby said sensor acts as a dosimeter and changes in the thickness of said chemical transduction layer alter said magnetic switching characteristics of said sensor dependent upon surrounding concentration of said selected chemical species.

* * * * *

UNITED STATES PATENT AND TRADEMARK OFFICE
CERTIFICATE OF CORRECTION

PATENT NO. : 5,821,129
DATED : October 13, 1998
INVENTOR(S) : Craig A. Grimes and William R. Seitz It is certified that error appears in the above-identified patent and that said Letters Patent is hereby corrected as shown below:

```
At Column 9, line 53, following
"being constructed" insert
-- from a --.
```

Signed and Sealed this

First Day of June, 1999

Attest:

Q. TODD DICKINSON

Attesting Officer

Acting Commissioner of Patents and Trademarks